US006409943B1

(12) United States Patent
Lavie et al.

(10) Patent No.: US 6,409,943 B1
(45) Date of Patent: Jun. 25, 2002

(54) IN-SITU-GENERATED SOLID RADIATION SOURCE BASED ON TUNGSTEN 188 /RHENIUM 188 AND USE THEREOF

(75) Inventors: Efraim Lavie, Mazkeret-Batia; Daniel Kijel, Rischon-Lezion; Eliahu Sayag, Holon; Yehoshua Michael Bettan, Metar, all of (IL)

(73) Assignee: The State of Israel, Atomic Energy Commission (IL)

( * ) Notice: Subject to any disclaimer, the term of this patent is extended or adjusted under 35 U.S.C. 154(b) by 0 days.

(21) Appl. No.: 09/557,130

(22) Filed: Apr. 25, 2000

Related U.S. Application Data

(63) Continuation-in-part of application No. 08/975,562, filed on Nov. 21, 1997, now abandoned.

(30) Foreign Application Priority Data

Nov. 3, 1997 (IL) .................................. 122094

(51) Int. Cl.$^7$ ....................... A61K 51/00; A61M 36/12; A61N 5/10; G21G 4/08
(52) U.S. Cl. .................... 252/644; 424/1.61; 600/3; 600/8
(58) Field of Search ................. 252/644; 424/1.61; 600/3, 6, 7, 8

(56) References Cited

U.S. PATENT DOCUMENTS

| | | | |
|---|---|---|---|
| 3,351,049 A | 11/1967 | Lawrence | 600/8 |
| 4,778,672 A | 10/1988 | Deutsch et al. | 424/1.1 |
| 4,859,431 A | 8/1989 | Ehrhardt | 423/2 |
| 4,889,707 A | 12/1989 | Day et al. | 424/1.1 |
| 5,145,636 A | 9/1992 | Vanderhevden et al. | 376/189 |
| 5,186,913 A | 2/1993 | Knapp, Jr. et al. | 423/2 |
| 5,213,561 A | 5/1993 | Weinstein et al. | 600/7 |
| 5,219,556 A | 6/1993 | Wolfangel | 424/1.1 |
| 5,382,388 A | 1/1995 | Ehrhardt et al. | 252/635 |
| 5,503,613 A | 4/1996 | Weinberger | 600/3 |
| 5,540,659 A * | 7/1996 | Teirstein | 604/104 |
| 5,728,042 A | 3/1998 | Schwager | 600/3 |
| 5,882,291 A | 3/1999 | Bradshaw et al. | 600/3 |
| 6,099,499 A * | 8/2000 | Ciamacco, Jr. | 600/3 X |
| 6,149,574 A * | 11/2000 | Trauthen et al. | 600/3 |

FOREIGN PATENT DOCUMENTS

EP 0 867 200 A2 9/1998

OTHER PUBLICATIONS

"The Merck Index", Stecher, Editor, 8th Ed., p. 916, 1968.
Lewington, V.J., "Targeted Radionuclide Therapy for Bone Metastases" EU.J.Nuc. Med. 20: 66–74 (1993).
Chinol, M. et al., Chemistry and Biological Behavior of Sm–153 and Re–186 Labeled Hydroxyapatite Particles, J. Nuc. Med. 34: 1536–1542 (1993).

* cited by examiner

Primary Examiner—Richard D. Lovering
(74) Attorney, Agent, or Firm—Lerner, David, Littenberg, Krumholz & Mentlik, LLP

(57) ABSTRACT

A radiotheraputical source of Rhenium$^{188}$ comprises metallic Tungsten$^{188}$ or a metal oxide of Tungsten$^{188}$. Therapeutic device using Rhenium$^{188}$ comprise a radioactive source for the in situ generation of Rhenium$^{188}$ from Tungsten$^{188}$.

35 Claims, 2 Drawing Sheets

IN-SITU-GENERATED SOLID RADIATION SOURCE BASED ON TUNGSTEN 188 /RHENIUM 188 AND USE THEREOF

FIELD OF THE INVENTION

This application is a Continuation-In-Part of application Ser. No. 08/975,562 filed Nov. 21, 1997, the disclosure of which is incorporated herein by reference.

The present invention relates to therapeutic radioactive sources, particularly radioactive sources utilizing Rhenium$^{188}$ as a therapeutic agent. More particularly, the invention relates to novel therapeutic devices employing a radioactive source generated in situ, from a solid metallic tungsten.

BACKGROUND OF THE INVENTION

The use of radiotherapy is quite common in modern medicine. Radiotherapy is used for a variety of uses, such as for post-surgery treatment of tumors, for various types of cancer therapy and, lately, the art has found that radiotherapy can be useful in preventing restenosis in patients treated for coronary diseases. Restenosis has been treated so far by short-term irradiation with radioactive sources located in catheters and wires, and by long-term irradiation with implanted devices, such as stents.

Many different radioactive materials have been used, including β and γ-emitters. In typical devices employed in the art, a radioactive portion is provided in a device to be inserted in a body cavity, in a variety of ways. In one method, the radioactive material is generated separately from the device, and attached thereto in a variety of ways, such as by containerization, coating, etc., and in other methods the device, e.g., a catheter, is irradiated shortly before use, to generate the radioactive material to be used for the treatment, and the device is then inserted into the body cavity.

The production of Rhenium$^{188}$ (Re$^{188}$) from Tungsten$^{188}$ (W$^{188}$) for pharmaceutical uses is described, e.g., in U.S. Pat. No. 5,382,388, U.S. Pat. No. 5,186,913, U.S. Pat. No. 5,145,636 and U.S. Pat. No. 4,778,672. According to the prior art Re$^{188}$ is generated in aqueous solution, and it must then be separated from the reagent, W$^{188}$, and complexed to organic and biological complexes prior to its injection into the body. Also, the prior art describes the use of tungsten oxide, where the tungsten is enriched W$^{186}$. Also large reaction volumes are described. The above chemistry limits the use of the product only to solutions and excludes the potential to apply it as a wire or coil for medical applications. The present invention describes the use of natural tungsten in a metal form. This configuration allows production of radioactive tungsten coil which generates in situ radioactive rhenium without the need to separate between the tungsten and the rhenium.

Another method of producing Re$^{188}$ is via the neutron activation of Re$^{187}$. However, purified Re$^{188}$ has a half life of about 17 hours, which is a very low shelf life for medical purposes. This means that, according to the prior art, in order to be able to use Re$^{188}$ in therapy, irradiation of the device must take place shortly before the surgical procedure takes place, which requires suitable and complex logistics for the hospital.

The present invention exploits the production of W$^{188}$ and its decay to Re$^{188}$, which are as follows:

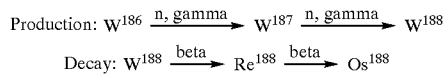

The half-life time ($t_{1/2}$) of W$^{188}$ is 69 days and Os$^{188}$ is stable. W$^{188}$ is prepared by a double neutron activation of W$^{186}$ target. The tungsten target is made from natural tungsten which has an abundance of 28.6% W$^{186}$ ("Table of Isotopes," Lederer, Hollander and Perlman, John Wiley & Sons.)

The advantages of using β-emitting sources are known in the art. Particularly, β-emitting sources have a limited depth of penetration in tissue and are therefore particularly suited for treatments, such as the prevention of restenosis, which do not require in-depth penetration and in which, in fact, in-depth penetration is undesirable. The β-emission of R$^{188}$ is suitable for penetration depth of 4–5 mm, in tissue, and the γ photons emission can be used to image the source within the body cavity. Furthermore, tungsten and rhenium have been used in medicine according to the known art, and no undesirable toxic effects have been disclosed to date (for toxicity see "The Merck Index," 1968, 8th Ed., p. 916).

Another important advantage of tungsten and rhenium is their high atomic number, which makes them excellent x-ray radio opaque markers. This feature is important for catheterization procedures and, even more, for non-opaque stents positioning within a vessel. Furthermore, in case of break or leak of part of the source, this x-ray contrast property enables the clinician to monitor its location and to attempt to retrieve it.

So far, however, the art has failed to provide a radioactive source which is convenient to use, which does not require expensive and hazardous irradiation procedures on the spot, and which provide the desired major proportion of β-emission, with only minor amount of γ-emission. Furthermore, the art has so far failed to provide such a source which, in addition to the above-mentioned desirable properties, is also relatively long-lived.

It is an object of the present, invention to provide a radioactive source for therapy, which overcomes the above-mentioned drawbacks of prior art sources.

It is another object of the invention to provide medical devices utilizing the source of the invention, which can be utilized in a variety of radiotherapy procedures, and particularly for the treatment and/or the prevention of restenosis.

It is a further object of the present invention to provide a long life Re$^{188}$ radioactive therapeutic device.

It is a still further object of the present invention to provide a method for the manufacture of a Re$^{188}$ radioactive therapeutic device that is free from the need to purify and to complex Re$^{188}$ prior to use.

It is a still further object of the present invention to provide a novel method of practicing radiotherapy by the use of Rhenium$^{188}$ as the source of radioactivity.

Other objects and advantages of the invention will become apparent as the description proceeds.

SUMMARY OF THE INVENTION

According to the present invention, W$^{188}$ is used in in situ generation of Re$^{188}$ for the purpose of radioactive therapy. Thus, the present invention provides a therapeutic device comprising a radioactive W$^{188}$/Re$^{188}$ source.

Preferably, the material of said source is tungsten metal. The source is. made of said material of coated with said material.

Preferably, the therapeutic device is coil-shaped and has a main body made of, or coated or implanted with, tungsten. In a preferred embodiment, it comprises a source wire having a $W^{188}/Re^{188}$ source at its distal tip. Also preferably, said radioactive source has a volume of not more than about 0.850 ml.

Preferably, said source wire is in the form of any of the group which consists of, but is not limited to, catheters, guidewires, stents or implants (pellet). Optionally, said source wire is made of tungsten or made of other suitable matter and coated with tungsten.

Preferably, the length of said source wire is between 1–50 mm, more preferably between 25–50 mm, and its diameter is between 0.2–10 mm, more preferably between 0.34–5 mm.

More preferably, when utilized in high "dose-rate" catheters, said source is 25–42 mm long, its diameter being between 0.34–0–8 mm; when utilized in stents, the source is 10–30 mm long, with a diameter of 0.7–3 mm, when utilized as interstitial implants the source is about 3–10 mm long with a diameter of about 0.3–1 mm, and when utilized as a round shape source, its diameter is about 3–10 mm. A "high dose-rate source" is defined as a source that can irradiate the target organ and achieve the desired dose in several minutes. Illustrative and non-limitative examples of suitable doses are those comprised between 1,500–5,000 rad; the activity is typically up to 100 mC, $W^{188}$ and the irradiation time is up to 30 minutes, more preferably up to 7 minutes.

Preferably, the W/Re source is within the activity range of 0.25 microcuries to 200 millicuries of $W^{188}/Re^{188}$.

In a preferred embodiment of the invention, the therapeutic device consists of or comprises a radioactive source consisting in a hollow coil made of $Tungsten^{188}$ wire, with wall thickness of not less than 75 pm. It has been found that this coil wall thickness enables complete self-absorption of the undesired Tungsten isotopes, e.g., $W^{188}$ and $W^{185}$ and complete in situ separation between Tungsten and the desired $Re^{188}$ isotope. The length of the radioactive source is up to 50 mm. In this specification and claims, the expression "in situ" indicates phenomena that take place in the therapeutic device itself The generation of $Re^{188}$, in this invention, takes place in the therapeutic device itself -in situ -in contrast to the prior art.

Thus, in a preferred embodiment, the present invention provides a therapeutic device comprising a source wire having a $W^{188}/Re^{188}$ source.

For coronary brachytherapy, the outer diameter of the radioactive source should be less than 0.8 mm in order to enable insertion via small coronary vessels. Further, the inner diameter of the radioactive source should not be less than 0.36 mm.

The radioactive $W^{188}/Re^{188}$ source is preferably encapsulated inside a polymeric tube and sealed. The polymeric tube may be sealed at both ends with sealant glue. To enable use of the source for several weeks without leak or contamination problems, both in storage and in use, the polymeric material should be resistant to a more than 100 mega-rad dose. Polyimides are satisfactory materials. Other satisfactory polymers are PVDF-polyvinylidenefluoride (Kynar), PI-polyimide and silicone rubber.

Another aspect of the invention is a method of practicing radiotherapy by the use of $Rhenium^{188}$ as the source of radioactivity, which comprises making a therapeutic device, as hereinbefore defined, by providing a source made of or coated with Tungsten and irradiating it, whereby to produce a radioactive solid source, allowing either undesirable short-lived gamma isotopes to decay or long-lived low-medium energy beta tungsten isotopes to be self-absorbed, introducing said source into or adjacent to the organ of the patient's body to be treated, and allowing $Rhenium^{188}$ to be generated in situ from the, irradiated Tungsten and to irradiate said organ by β-emission.

DETAILED DESCRIPTION OF THE INVENTION

Figure 1A:
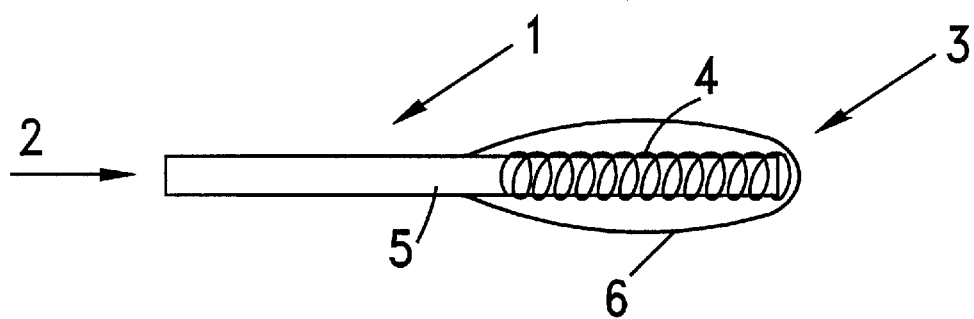
FIGS. 1A and 1B schematically illustrate the positioning of a radioactive source, respectively on or inside a catheter.

In one aspect, the invention is directed to a radiotherapeutical source of $Rhenium^{188}$ comprising metallic $Tungsten^{188}$. Thus, the invention provides for the first time a means to generate β-radiation from a $Rhenium^{188}$ source, for an extended period of time, at a constantly predictable rate, from a pre-irradiated solid metallic Tungsten source. Apart from the aforementioned advantage of excellent logistic for the hospital, the catheter of the invention, comprising the W/Re irradiation system, has the added advantage of being reusable, so that the same catheter can be transferred from one patient to the other. In the prior art, $Re^{188}$ is produced in portions and decays once it is produced, with short half-life (17 hours). In the present invention, $Re^{188}$ is produced continuously, as long as $W^{188}$ is present, and its production is dominated by the presence of $W^{188}$, which has a half-life of 69 days.

In another aspect, the invention is directed to a therapeutic device comprising a radioactive source for the in situ generation of $Rhenium^{188}$ from $Tungsten^{188}$.

Many different therapeutic devices can be made according to the invention. Illustrative and non-limitative examples of useful devices include catheters, guidewires, stents and implants.

According to a preferred embodiment of the invention, the therapeutic device comprises a main body at least a portion of which consists of, or is coated with, or houses, a radioactive. source for the in situ generation of $Rhenium^{188}$ from metallic $Tungsten^{188}$. The irradiation of the W source for a catheter is carried out as follows: the W coil is loaded in a quartz capsule, or in a graphite can, typical dimensions being 9 mm diameter and 45 mm length, or alternatively in aluminum cans or in graphite cans, typical dimensions being 8–23 mm diameter and 70 mm length. The cans or capsules are positioned in the reactor core and irradiated. Homogeneity of the flux is obtained by rotating the sample during irradiation. The decay of the source activity with time is illustrated in Table I. $Re^{188}$ activity decay with time is illustrated in Table II.

TABLE I

Source Activity Decay with Time - $W^{188}$

| Time (days) after irradiation | % of original activity |
|---|---|
| 0 | 100 |
| 69 | 50 |
| 138 | 25 |

TABLE II

Activity Decay with Time - $Re^{188}$

| Time (hours) after irradiation | % of original activity |
|---|---|
| 0 | 100 |
| 17 | 50 |
| 34 | 25 |
| 51 | 12.5 |

From the above tables it can be seen that in the $W^{188}$-$Re^{188}$ system the time is dominated by $W^{188}$, since $W^{188}$ decays much more slowly than $Re^{188}$.

According to a preferred embodiment of the invention, there is provided a therapeutic device wherein the radioactive source is located at its distal end. Such devices can be made of a variety of materials, as will be appreciated by persons skilled in the art. A preferred construction for the therapeutic device is that in which the main body is made of, or coated with, metallic tungsten. However, it should be understood that the invention is by no means limited to any particular construction material or combination of materials for the therapeutic device.

According to a preferred embodiment of the invention the in situ-generated source of Rhenium$^{188}$ is in the form of a device selected from among wires, coils, springs, seeds, powders or pellets encapsulated in an outer shell.

When used for vascular brachytherapy, the device can be inserted into a sterile closed-end lumen catheter (for example made by Cordis, Inc., a Johnson & Johnson company) and thus can avoid contact with blood. This configuration can enable using the same source for a plurality of patients. In one example of therapeutic device the length of the source is between about 25 mm and 50 mm. When the therapeutic device of the invention is a catheter, it may typically have a length of between about 25 mm and 50 mm, and a diameter between 0.34 mm and 0.80 mm. When the therapeutic device of the invention is a stent, it may typically have a length of between about 10 mm and 30 mm, and a diameter of between about 0.7 mm and 3 mm.

When the therapeutic device of the invention is an interstitial implant, it may typically have a length of about 5 mm. and a diameter of about 0.4–1 mm. When the therapeutic device according to the invention is a round shaped source it may typically have a diameter of about 3–7 mm.

The activity of the source may change according to the specific use for which it is designed. Illustrative and non-limitative therapeutic devices may comprise a source having an activity of between 0.25 microcuries to 100 millicuries of $W^{188}$.

The invention also encompasses the use of solid Tungsten$^{188}$ as a precursor for the in situ generation of therapeutically active Rhenium$^{188}$. As stated, the source for the in situ generation of Rhenium$^{188}$ from Tungsten $^{188}$, is preferably a coil and will be described as such hereinafter, but may have another structure. The coil is made of solid tungsten or of any other suitable material that is coated with tungsten. Said coil is cleaned by means, e.g., of washing with ethanol and heat-drying. The coil is then irradiated, in order to produce a radioactive source coil. In many cases, the source coil is not utilized immediately after its irradiation, in order to allow short-lived isotopes, which may be undesirable in therapy, to decay. The tungsten wall of the coil, that acts as the $Re^{188}$ source, should always have a certain thickness, preferably of at least 75 μm. The same total coil wall thickness is required of the tungsten coating, if the source is coated with and not made of tungsten.

In case that the source coil is a catheter-based system, the radioactive coil source segment can be mounted on or inside. a catheter in a hot cell and be sealed, e.g., by a heat-shrinkable polymer (polyester), or by a suitable sealant (glue), like Loctite 416.

In case that the source coil is in the form of a stent, known stents such as a titanium or Nitinol stent can be coated with tungsten for the purposes of the present invention, or specifically manufactured stents can be provided, using tungsten as a construction material. In the first case, about 1–10 micrograms of natural solid W should be implanted at about 0.2 μm depth in the stent surface, so that leaking of radioactivity is minimized and the β-radiation is not absorbed. The required activity range in a stent is between 0.24 and 40 microcuries.

The high activity level catheter sources are useful in one-time short irradiation time treatments, such as in preventing the restenosis in coronary arteries (PTCA), or for eye treatments. The acceptable dose for this purpose is 15–25 Gy (1500–2500 rad) at a distance of 2 mm from the source center. This dose can typically be achieved in 3–10 minutes of irradiation.

The present invention is especially useful in applications with required depth of penetration of 4–5 mm with a minimal damage to healthy tissues. This result cannot be achieved using some of the γ and x-ray sources acceptable in therapy.

The use of $W^{188}$ is convenient and flexible, rendering it attractive for use in hospitals. $W^{188}$ can be produced in high or hyper flux reactors without the need for cyclotrons as in the case of P-32 and V-48 implanted stents.

As will be appreciated by the skilled person, the use of radiotherapy in general, and the use of β-radiation in particular, is well known in the art. Furthermore, the use of radiotherapy for the purposes to which the present invention is directed is also well known. Therefore, no detailed discussion of medical and therapeutic aspects is made herein, for the sake of brevity, and the reader is referred to the many publications dealing with the medical aspects of, e.g., restenosis and its prevention by radiotherapy, such as V. J. Lewington, *Eu. J Nuc. Med.* 20, 66–74 (1993), "Targeted Radionuclide Therapy for Bone Metastases"; or M. Chinol et al., *J Nuc. Med.* 34, 1536–1542 (1993), "Chemistry and Biological Behaviour of Sm-153 and Re-186 Labeled Hydroxyapatite Particles."

A major problem of extensive leakage (5–25%) was registered when using radionuclides as a $Re^{186}$, $Sr^{89}$ and others for radiation synovectomy. According to the present invention a solid source of W/Re will be on the one hand effective in treating the synovial joint and on the other hand will exhibit minimal extra-articular leakage of radioactivity.

Figure 1B:
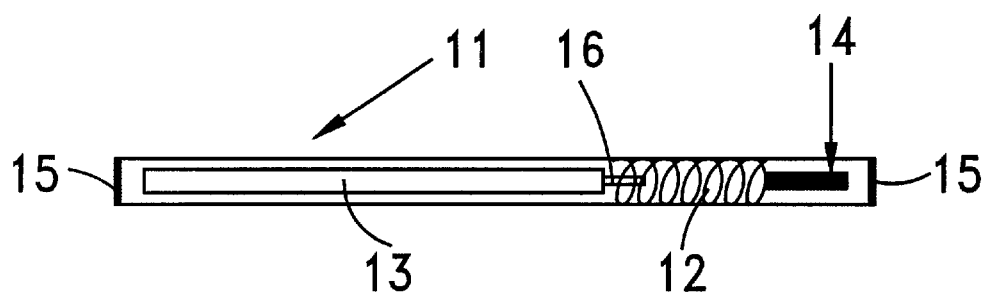

FIGS. 1A and 1B schematically illustrate the positioning of a radioactive source on and inside a catheter. FIG. 1A shows a catheter, generally indicated by numeral 1, which is shown truncated at extremity 2. The catheter is provided at its distal end 3 (shown in cross-section along the axis of the catheter) with a tungsten coil .4, which is the radioactive source. The coil 4 is coiled around elongated portion 5 of catheter 1, and is encapsulated by an external sheath, 6, which may be of any suitable material, e.g., plastic or metal. Said coil is hollow and may have, e.g., a length of 40 mm and an outer diameter of 0.55 mm and an inner diameter of 0.30 mm.

FIG. 1B shows a catheter 11, made of a polymer such as a polyimide, and having, e.g., an outer diameter of 0.70 mm and an inner diameter of 0.60 mm, and a length of 260 cm, in which is inserted a tungsten coil 12 having, e.g., a diameter of 0.55 mm, a length of 40 mm and a wall thickness of 0.127 mm. 1 is a Nitinol guidewire having, e.g., a length of 260 mm and tapered at 16 from a diameter of 0.36 mm to a diameter of 0.25 mm at its distal end. The ends 15 of the catheter are sealed, e.g., with a glue such as Metca-100 or Loctite 416. 14 is an 8 mm silicone rubber spacer and it is inserted between the coil edge and the seal to protect the seal from irradiation damage. Most of the beta dose in the longitudinal axis is blocked by this spacer.

Figure 2:
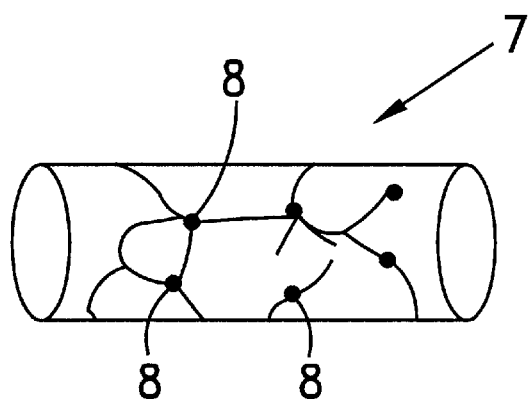
FIG. 2 shows a stent made of metal wire and provided with a plurality of implanted radioactive elements.

FIG. 2 shows a stent 7, made of metal wire and provided with a plurality of implanted radioactive elements, 8, three of them being indicated in the figure.

Figure 3:
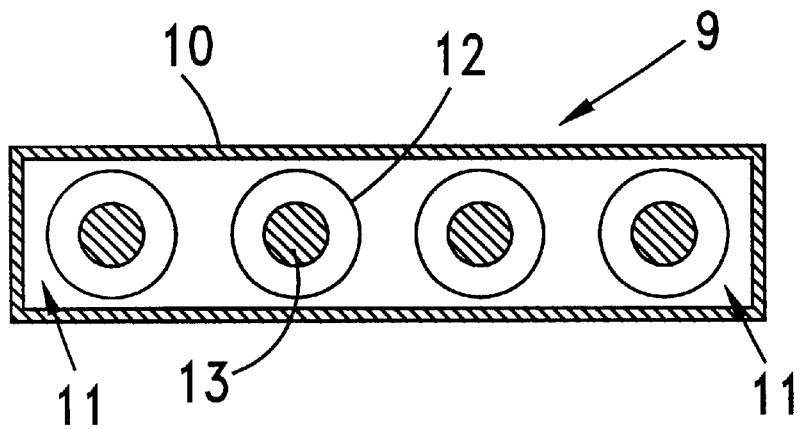
FIG. 3 schematically illustrates an implant according to one preferred embodiment of the invention.

FIG. 3 schematically illustrates an implant according to one preferred embodiment of the invention. Implant 9, which in this particular example has a cylindrical form, consists of a tube 10, which may be of any suitable material, which tube houses a plurality of pellets 11. The tube and the pellets of FIG. 3 are shown in longitudinal cross-section. Each pellet 11 consists of an outer shell 12, which is typically made of titanium, and of a radioactive $W^{188}/Re^{188}$ core 13.

Figure 4A:
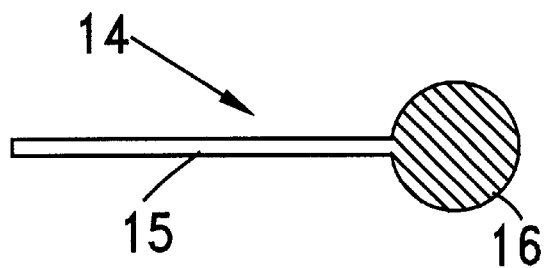
FIGS. 4A & 4B schematically illustrate applicators of radioactive sources which are particularly suitable for eye therapy.
Figure 4B:
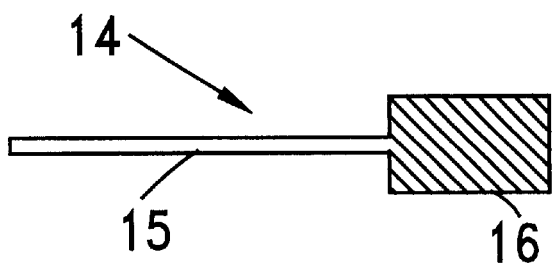

FIG. 4 schematically illustrate applicators of radioactive sources which are particularly suitable for eye therapy, FIG. 4A showing a round shaped applicator, and FIG. 4B a rod-shaped one. The applicator, 14, simply consists of a handle 15 at the end of which there is provided a radioactive source 16, in any suitable shape, e.g., round or rod-like.

The above and other characteristics and advantages of the invention will become apparent through the following illustrative and non-limitative examples of preparation.

EXAMPLE 1

Natural tungsten $W^{186}$ coil was prepared from a tungsten wire having a purity of 99.95%, and a diameter of 0.075–0.2 mm. The coil was 30–40 mm long and had an outer diameter of about 0.8 mm, and weighed about 110 mg. The coil was washed with water and alcohol in an ultrasonic bath in order to remove impurities. After the wash the coil was dried by heating in vacuum to 1000° C. for 20 hours. The coil was then kept in a sealed container until used.

EXAMPLE 2

A coil prepared according to Example I is neutron irradiated in a high flux reactor for about 21 days with thermal neutron flux of about $1.5*10^{15}$ neutrons/$cm^2$*sec to produce about 200 millicuries of $W^{18}/Re^{188}$. Also approximately 1.6 Curies of $W^{185}$ were produced. The coil is not used for 3 weeks subsequent to its irradiation, in order to allow short-lived isotopes to decay. The dosimetry is determined by a Ge spectrometer and the activity by a Capintec dose calibrator.

EXAMPLE 3

An irradiated coil (source) of Example 1 is mounted on a 260 cm polyimide catheter or Nitinol guidewire on its distal end and encapsulated by heat-shrink polymer.

EXAMPLE 4

An irradiated tungsten solid coil source is inserted into the distal end of a polyimide catheter (260 cm length). The outer dimensions of the catheter are 0.65–0.75 mm and inner diameter 0.60 mm. After the "hot" coil assembly, a Nitinol guidewire is inserted inside the catheter. This guidewire is 0.36 mm in diameter, and is tapered to 0.25 mm in its distal end. The coil is stopped by this guidewire. Then, both ends of the catheter are sealed by Metca 100 or Loctite 416 glues. To avoid irradiation damage to the seal, there is an 8 mm silicone rubber spacer between the source edge and the sealant. This configuration proved to be radioactive leak-proof. This structure has been demonstrated in animals to have excellent pushability and tractability.

EXAMPLE 5

A 30 mm long support titanium or Ni/Ti (Nitinol) guidewire, having a diameter of 0.36 mm is homogeneously electroplated with 115 mg of natural W. The coated wire is treated and irradiated as in Examples 1 and 2. The 30 mm source is linked to a 260 cm Ti or Ni/Ti guidewire having a diameter of 0.36 mm (0.014"), by thrusting or screwing or welding.

EXAMPLE 6

A 30–40 mm long support of Ni/Ti (Nitinol) wire having a diameter of 0.7 mm (0.027") is electroplated as in Example 5.

EXAMPLE 7

A 260 cm long titanium or Ni/Ti (Nitinol) wire, having a diameter of 0.7 mm (0.027") is electroplated as in Example 5 and treated and irradiated as in Examples 1 and 2.

EXAMPLE 8

A titanium or Nitinol stent is electroplated as in Example 5 and treated and irradiated as in Examples 1 and 2.

The above description and examples have been provided for illustrative purposes only, and are not intended to limit the invention in any way. As will be apparent to the skilled person, many modifications, variations and adaptations may be made to the invention by persons skilled in the art, without departing from the spirit of the invention or exceeding the scope of the claims.

What is claimed is:

1. A method of making a therapeutic device comprising providing a radioactive solid source made of or coated with solid Tungsten metal and irradiating said source to produce a radioactive source for the in situ generation of $Rhenium^{188}$ from $Tungsten^{188}$.

2. A therapeutic device comprising a radioactive solid source for the in situ generation of $Rhenium^{188}$ from $Tungsten^{188}$, wherein said radioactive source is made of solid Tungsten metal.

3. A therapeutic device according to claim 2, wherein said radioactive source has a volume of not more than 0.850 ml.

4. A therapeutic device according to claim 2, comprising a device selected from the group consisting of catheters, guidewires, stents and implants.

5. A therapeutic device according to claim 4, comprising a stent, having a length of between about 10 mm and 30 mm, and a diameter of between about 0.7 mm and 3 mm.

6. A therapeutic device according to claim 4, comprising an interstitial implant, having a length of about 3–10 mm and a diameter of about 0.3–1 mm.

7. A therapeutic device according to claim 2, wherein the source has a length from 1 to 50 mm and a diameter from 0.2 to 10 mm.

8. A therapeutic device according to claim 2, including a distal end and a proximate end, and wherein the radioactive source is located at said distal end.

9. A therapeutic device according to claim 1, comprising a source coil having a distal end, and wherein said $W^{188}/Re^{188}$ source is at its distal end.

10. A therapeutic device according to claim 2, wherein the radioactive source for the in situ generation of $Re^{188}$ from $W^{188}$ is in the form of a device selected from the group-consisting of wires, coils, springs, seeds, powders and pellets encapsulated in an outer shell.

11. A therapeutic device according to claim 2, comprising a catheter, having a distal end and having a radioactive source at its distal end, said source having a length of between 25 mm and 50 mm, and a diameter of between 0.34 mm to 0.8 mm.

12. A therapeutic device according to claim 11, wherein said catheter includes a seal and a silicone rubber spacer inserted inside the catheter to protect the seal from irradiation damage.

13. A therapeutic device according to claim 2, comprising a round shaped source having a diameter of about 3–10 mm.

14. A therapeutic device according to claim 2, comprising a solid tungsten source having an activity of between 0.25 microcuries to 200 millicuries $W^{188}/Re^{188}$.

15. A therapeutic device according to claim 2, wherein the radioactive source is encapsulated within a polymeric tube and sealed with sealant glues at both ends.

16. A therapeutic device according to claim 15, wherein the polymeric tube is made of a polyimide.

17. A therapeutic device according to claim 16, wherein a tapered Ni/Ti guidewire is inserted into the polymeric tube.

18. A therapeutic device comprising a radioactive solid source for the in situ generation of $Rhenium^{188}$ from $Tungsten^{188}$, wherein said radioactive solid source is a hollow coil made of Tungsten wire, said hollow coil having a wall thickness of not less than 75 $\mu$m.

19. A therapeutic device according to claim 18, for use in coronary brachytherapy, wherein the outer diameter of the radioactive source coil is less than 0.8 mm and the inner diameter thereof is not less than 0.36 mm.

20. A therapeutic device comprising a radioactive solid source for the in situ generation of $Rhenium^{188}$ from $Tungeten^{188}$, wherein said radioactive source is coated with Tungsten metal.

21. A therapeutic device according to claim 20, wherein said radioactive source has a volume of not more than 0.850 ml.

22. A therapeutic device according to claim 20, comprising a device selected from the group consisting of catheters, guidewires, stents and implants.

23. A therapeutic device according to claim 22, comprising a stent, having a length of between about 10 mm and 30 mm, and a diameter of between about 0.7 mm and 3 mm.

24. A therapeutic device according to claim 22, comprising an interstitial implant, having a length of about 3–10 mm and a diameter of about 0.3–1 mm.

25. A therapeutic device according to claim 20, wherein the source has a length from 1 to 50 mm and a diameter from 0.2 to 10 mm.

26. A therapeutic device according to claim 20, including a distal end and a proximate end, and wherein the radioactive source is located at said distal end.

27. A therapeutic device according to claim 20, comprising a source coil having a distal end, and wherein said $W^{188}/Re^{188}$ source is at its distal end.

28. A therapeutic device according to claim 20, wherein the radioactive source for the in situ generation of $Re^{188}$ from $W^{188}$ is in the form of a device selected from the group consisting of wires, coils, springs, seeds, powders and pellets encapsulated in an outer shell.

29. A therapeutic device according to claim 20, comprising a catheter, having a distal end and having a radioactive source at its distal end, said source having a length of between 25 mm and 50 mm, and a diameter of between 0.34 mm to 0.8 mm.

30. A therapeutic device comprising a radioactive solid source for the in situ generation of $Rhenium^{188}$ from $Tungsten^{188}$, wherein said radioactive solid source comprises a round shaped source having a diameter of about 3–10 mm.

31. A therapeutic device comprising a radioactive solid source for the in situ generation of $Rhenium^{188}$ from $Tungsten^{188}$, wherein said radioactive source is encapsulated within a polymeric tube and sealed with sealant glues at both ends.

32. A therapeutic device according to claim 31, wherein the polymeric tube is made of a polyimide.

33. A therapeutic device according to claim 32, wherein a tapered Ni/Ti guidewire is inserted into the polymeric tube.

34. A therapeutic device comprising a radioactive solid source for the in situ generation of $Rheniun^{188}$ from $Tungsten^{188}$, said device comprising a catheter having a distal end and having a radioactive source at said distal and, said source having a length of between 25 mm and 50 mm, and a diameter of between 0.34 mm to 0.8 mm, wherein said catheter includes a seal and a silicone rubber spacer inserted inside the catheter to protect the seal from irradiation damage.

35. A method of practicing radiotherapy by the use of $Rhenium^{188}$ as the source of radioactivity, comprising making a therapeutic device by providing a source made of or coated with solid Tungsten metal and irradiating said source to produce a radioactive solid source, allowing undesirable short-lived isotopes to decay or long-lived tungsten isotopes to be self-absorbed, introducing said source into or adjacent to an organ of a patientIs body to be treated, and allowing $Rhenium^{188}$ to be generated in situ from the irradiated Tungsten and to irradiate said organ by β-emission.

* * * * *

UNITED STATES PATENT AND TRADEMARK OFFICE
CERTIFICATE OF CORRECTION

PATENT NO. : 6,409,943 B1
DATED : June 25, 2002
INVENTOR(S) : Efraim Lavie, Daniel Kijel, Eliahu Sayag, Yehoshua Michael Bettan, Theodor Morel Fishler and Salomone Antebi It is certified that error appears in the above-identified patent and that said Letters Patent is hereby corrected as shown below:

Column 1,
Line 2, "1997, the" should read -- 1997 and now abandoned, the --.

Column 2,
Line 43, "present, invention" should read -- present invention --.

Column 3,
Line 2, "is. made" should read -- is made --.
Line 37, "75 pm" should read -- 75 $\mu$m --.
Line 44, "itself The" should read -- itself. The --.

Column 4,
Line 9, "the, irradiated" should read -- the irradiated --.
Line 53, "radioactive. source" should read -- radioactive source --.

Column 7,
Line 18, "1 is a Nitinol" should read -- 13 is a Nitinol --.

Column 9,
Line 13, "claim 1" should read -- claim 2 --.

Column 10,
Line 43, "distal and" should read -- distal end --.
Line 56, "patientls body" should read -- patient's body --.

Signed and Sealed this

Fifth Day of November, 2002

Attest:

Attesting Officer

JAMES E. ROGAN
Director of the United States Patent and Trademark Office